US00PP31915P2

(12) United States Plant Patent
Valin

(10) Patent No.: US PP31,915 P2
(45) Date of Patent: Jun. 30, 2020

(54) ***WEIGELA* PLANT NAMED 'TMWG16-04'**

(50) Latin Name: *Weigela florida*
Varietal Denomination: TMWG16-04

(71) Applicant: Branded Garden Products Ltd., Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 0 days.

(21) Appl. No.: 16/501,910

(22) Filed: Jul. 2, 2019

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new variety of *Weigela* plant named 'TMWG16-04' that is characterized by upright narrow vase-shaped plant habit, scarlet flowers which are borne profusely and continuously in mid to late-spring and then sporadically during summer, in clusters along the entire length of the stem, is disclosed.

3 Drawing Sheets

Genus and species: *Weigela florida.*
Variety denomination: 'TMWG16-04'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG16-04'.

Whereas varieties of *Weigela florida* in commerce have typically been bred for low compact plant habit, 'TMWG16-04' was developed and selected by the inventor for its unique combination of upright plant habit and profuse flowering along the entire stem.

'TMWG16-04' resulted from the open-pollination in Summer 2014 in Ipswich, Suffolk, United Kingdom of the inventor's proprietary seedling *Weigela florida* 'WG13003' (female parent, unreleased and unpatented) with a population of possible male parents that had been raised by the inventor from the open pollination of *Weigela florida* plant 'Alexandra' (U.S. Plant Pat. No. 10,772). 'TMWG16-04' was selected in 2016 in Ipswich, Suffolk, United Kingdom. 'TMWG16-02' was grown at a greenhouse and field nursery in Ipswich, Suffolk, United Kingdom.

'TMWG16-04' was asexually reproduced in 2016 in Ipswich, Suffolk, United Kingdom by softwood cuttings. Since that time, the unique characteristics of the new *Weigela* plant have been uniform, stable and reproduced true to type in successive generations of asexual reproduction via softwood cuttings.

SUMMARY

The following traits have been repeatedly observed and represent the characteristics of 'TMWG16-04'. 'TMWG16-04' has not been tested under all possible conditions and phenotypic differences may be observed with variations in environmental, climatic and cultural conditions, however, without any variance in genotype.

1. 'TMWG16-04' exhibits an upright narrow vase-shaped plant habit.
2. After two years of growth in a 3-gallon container, plants of 'TMWG16-04' achieve a height of 100 cm to 125 cm and a width (at full height) of 50 cm to 60 cm.
3. A mature plant of 'TMWG16-04' which is growing in-ground achieves a height of 180 cm to 200 cm and a width at full height of 90 cm to 120 cm.
4. The flowers of 'TMWG16-04' are scarlet in color.
5. The flowers of 'TMWG16-04' are borne in clusters along the entire length of the stem.
6. 'TMWG16-04' flowers profusely and continuously in mid to late-spring and then sporadically during summer.
7. The foliage of 'TMWG16-04' is mid green in color.
8. 'TMWG16-04' grows well in moist well-drained soils in full sun to partial shade.
9. 'TMWG16-04' is hardy at least to USDA Zone 6.

BRIEF DESCRIPTION OF THE PHOTOGRAPHS

The accompanying color photographs illustrate the overall appearance of the new *Weigela* variety 'TMWG16-04' showing colors as true as it is reasonably possible to obtain in colored reproductions of this type. Colors in the photographs may differ from the color values cited in the detailed botanical description, which accurately describe the actual colors of the new variety 'TMWG16-04'.

Figure 1:
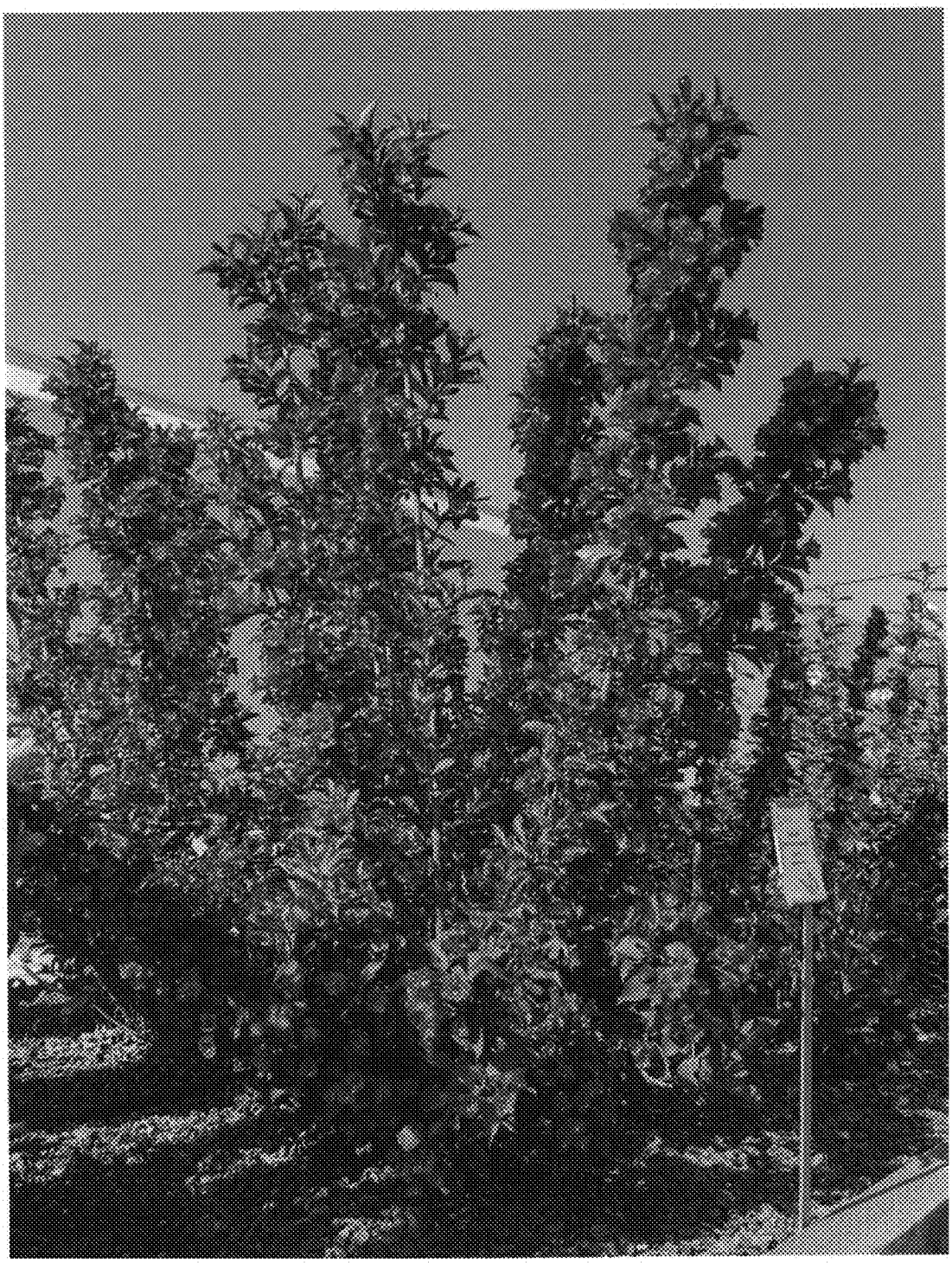
FIG. 1 depicts a row of three-year old plants of 'TMWG16-04' which are growing in open ground in Oxnard, Calif.
Figure 2:
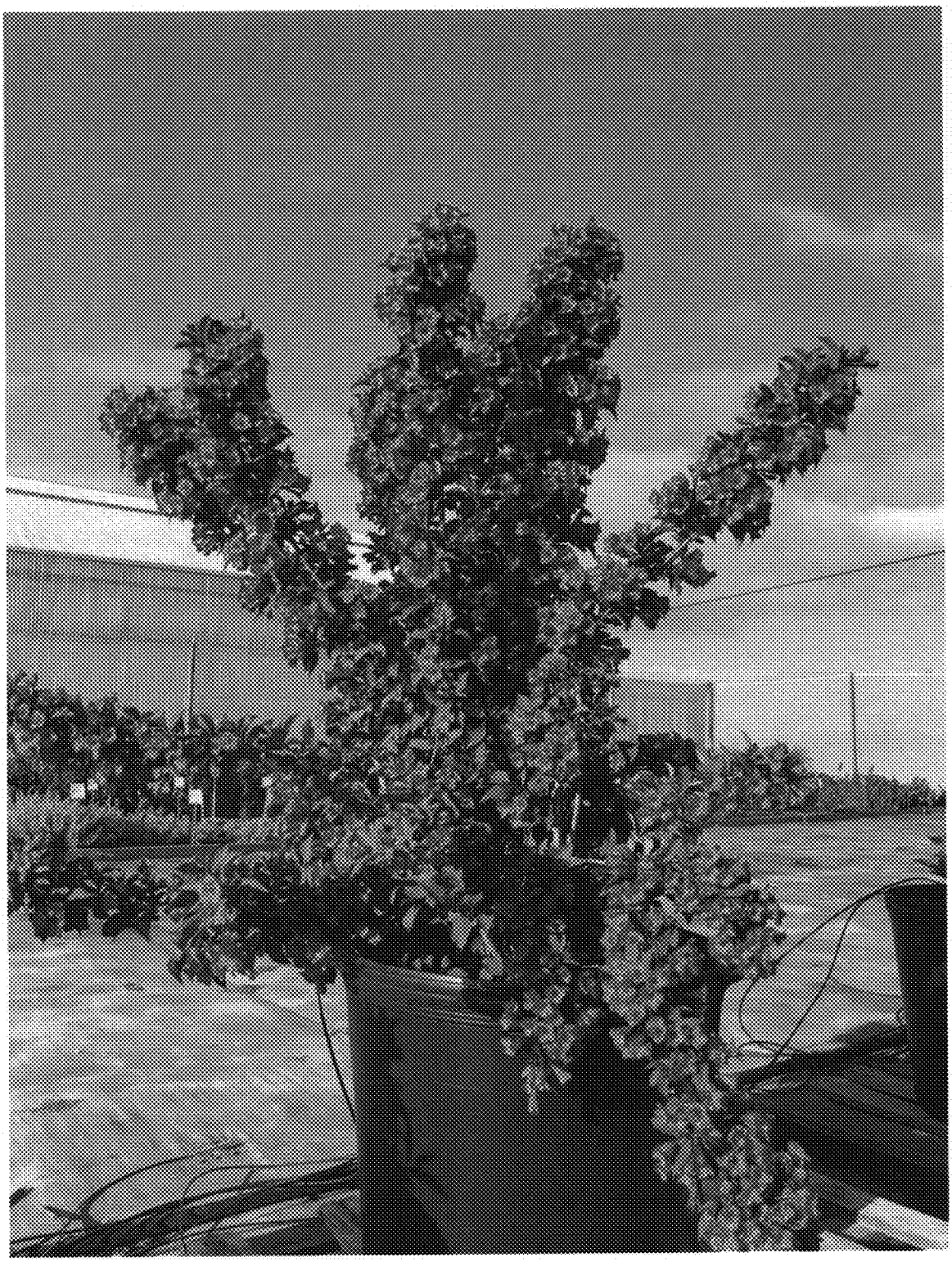
FIG. 2 depicts a two-year old flowering plant of 'TMWG16-04' which is growing out of doors in a 3-gallon container in Oxnard, Calif.
Figure 3:
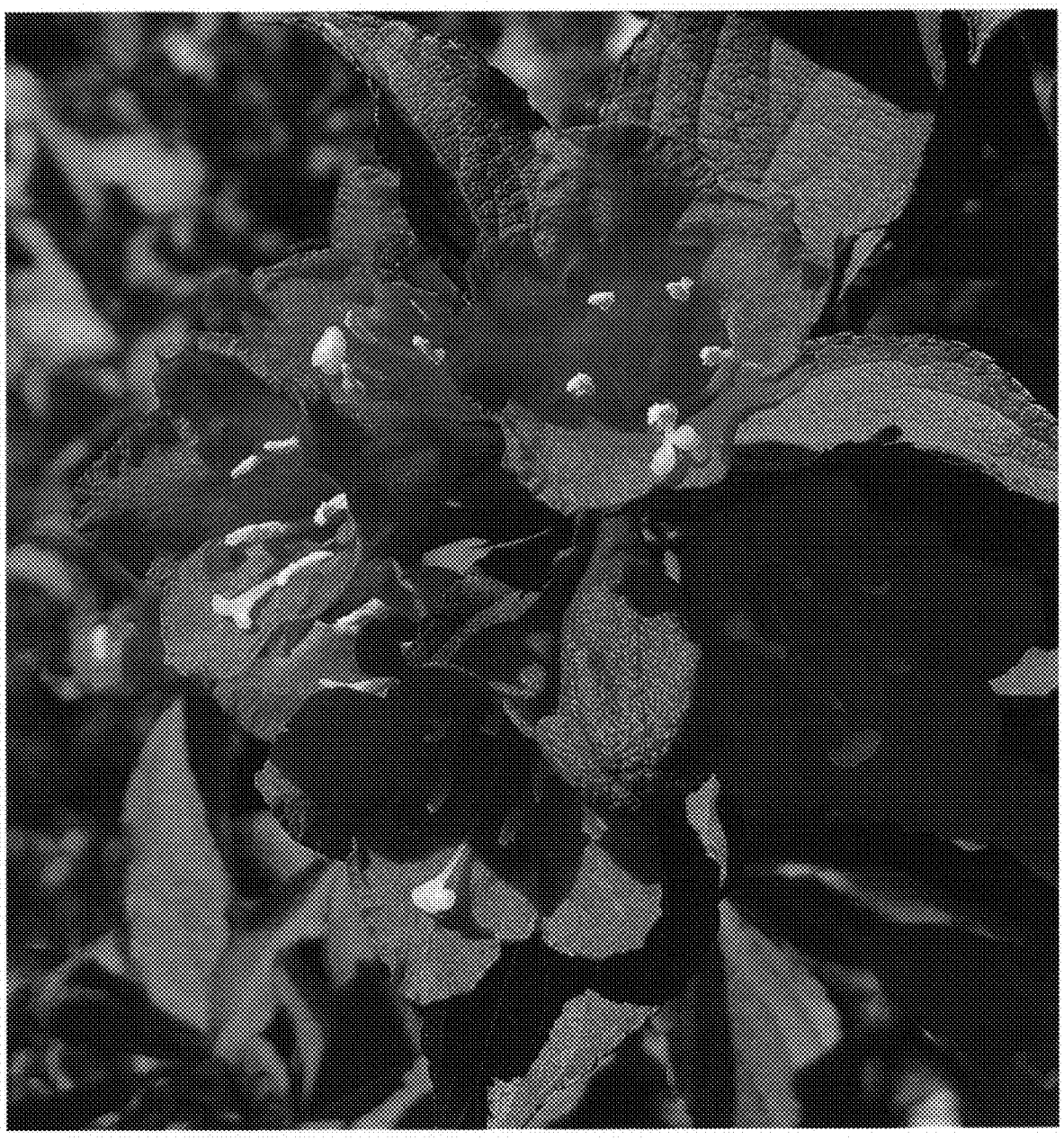
FIG. 3 depicts a cluster of buds and flowers of 'TMWG16-04'.

Photographs were taken in Oxnard, Calif. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new variety 'TMWG16-04'. Data was collected from two-year old plants grown outdoors in 3-gallon containers in Oxnard, Calif. The color determinations are in accordance with the 2007 edition of The Royal Horticultural Society Colour Chart of The Royal Horticultural Society, London, England, except where general color terms of ordinary dictionary significance are used. No chemicals were used to treat the plants. Growing conditions are typical of the genus *Weigela*.

Botanical classification: *Weigela*.

*Variety*.—'TMWG16-04'.

*Species*.—*Florida*.

Parentage: 'TMWG16-04' was raised from seed collected from *Weigela florida* 'WG13003' as open-pollinated female parent. The unknown male parent was raised from the open-pollination of *Weigela* 'Alexandra'.

Plant description:

*Growth habit*.—Upright, narrow vase shaped.

*Use*.—In containers and in the landscape. May be grown on canes or on a trellis to produce a more markedly columnar plant habit.

*Suitable container sizes*.—1 to 3-gallon containers.

*Dimensions in second year (the observed plants) in a 3-gallon container*.—100 cm to 125 cm in height, and 50 cm to 60 cm. in width measured at full plant height.

*Dimensions when mature in open ground*.—180 cm to 200 cm in height, 90 cm to 120 cm in width measured at full plant height.

*Hardiness*.—At least USDA Zone 6.

*Propagation*.—Stem cuttings.

*Time to initiate roots*.—5 to 6 weeks are required to produce roots on an initial cutting.

*Crop time*.—One year to 18 months are required to produce a finished one-gallon to three-gallon container from a rooted cutting.

*Root system*.—Fibrous.

*Light*.—Plant in full sun or partial shade.

*Soil*.—Plant in moist but well drained soil.

*Type*.—Deciduous shrub.

*Seasonal interest*.—Vibrant scarlet flowers in spring and summer.

Stem:

*Shape*.—Terete.

*Dimensions*.—15 cm to 20 cm in length, 1 cm diameter at soil level.

*Color*.—198A.

*Surface*.—Lignified in second year, rough, glabrous, lenticels present.

*Lenticels*.—spaced approximately 5 mm apart, roughly circular, diameter 2 mm, raised 1 mm, color is 196C.

Branches:

*Branch stem dimensions*.—65 cm to 100 cm in length, 5 mm to 8 mm in diameter.

*Shape*.—Square with rounded edges.

*Internode length*.—6 cm to 8 cm.

*Color*.—178B.

*Surface*.—Smooth, pubescent with short fine white hairs.

Foliage:

*Leaf arrangement*.—Opposite.

*Leaf division*.—Simple.

*Leaf shape*.—Ovate, slightly recurved.

*Leaf attachment*.—Sessile or very short petiolate.

*Petiole dimensions (where present)*.—2 mm in length and 2 mm in width.

*Petiole color*.—Ranges between 137B and 138B.

*Leaf dimensions*.—90 mm in length, 37 mm in width.

*Leaf surface (adaxial)*.—Glabrous.

*Leaf surface (abaxial)*.—Glabrous, pubescent, hairs fine, length 1 mm to 2 mm, white.

*Leaf color, spring and summer (adaxial surface)*.—137B.

*Leaf color, spring and summer (abaxial surface)*.—138B.

*Leaf color, fall (both surfaces)*.—Initially 139C then ranging through N144B, 151A to 163B.

*Leaf apex*.—Acute, occasionally acuminate.

*Leaf base*.—Rounded.

*Leaf margin*.—Finely serrate, glabrous except leaf margin pubescent towards base, hair color white, hair length 1 mm to 2 mm.

*Leaf venation pattern*.—Pinnate.

*Veins (adaxial surface)*.—Prominent midrib, slightly depressed, color 155A.

*Veins (abaxial surface)*.—Prominent midrib and lateral veins, raised approximately 1 mm, color ranges between 155A and 160C.

Inflorescence:

*Inflorescence form*.—Cymose. Present at each leaf axil.

*Quantity of flowers per inflorescence*.—5 to 8.

*Time and duration of flowering*.—Beginning in April or May, peak flowering in May and June, continuing sporadically until July.

Flowers:

*Flower aspect*.—Salverform.

*Diameter of fully developed flower*.—25 mm to 28 mm.

*Length of flower*.—35 mm.

*Bud*.—Shape: Cylindrical, apex capitate. Color: 60B. Dimensions: 25 mm to 30 mm in length, 8 mm to 10 mm immediately prior to opening. Surface: Rugose.

*Bracteoles*.—Arrangement: Uneven pair located at the base of peduncle. Shape: Narrowly lanceolate. Dimensions: Longer bracteole 8 mm to 12 mm in length, 1 mm in width; shorter bracteole 5 mm to 7 mm in length, 1 mm in width. Color: 181B. Surface: Glabrous.

*Peduncle*.—Dimensions: 20 mm in length and 1.5 mm in diameter. Shape: Terete. Color: 178B. Surface: Puberulent, hairs fine, white.

*Calyx, sepals*.—Shape: Funnel-shaped. Calyx diameter: 7 mm at sepal apex. Sepals: 5 in number, irregularly fused. Sepal dimensions: 10 mm to 12 mm in length, 3 mm in width. Sepal color (adaxial surface): 148A with longitudinal streaks 60B. Sepal color (abaxial surface): 148A. Sepal surface (both surfaces): Puberulent, hairs fine, white.

*Corolla*.—Shape: Salverform. Dimensions: 35 mm in length, 2 mm in diameter at base, 12 mm in diameter at base of petal lobes. Surface: Both surfaces glabrous, adaxial slightly longitudinally corrugated.

Tube color (adaxial surface): 60B. Tube color (abaxial surface): 60D. Petals (lobes): Number: 5, fused. Shape: Equal, orbicular. Color (adaxial surface): 60B. Color (abaxial surface): 60D. Surface texture: Adaxial surface smooth, margins rugose. Abaxial surface rugose.

Reproductive organs:

*Number of stamens.*—5, fused at base and lower half fused to corolla tube.

*Dimensions.*—20 mm in length and 1.5 mm in diameter.

*Filament color.*—54A.

*Anther shape.*—Bifid, narrow elliptical.

*Anther dimensions.*—4 mm to 5 mm in length and 1 mm in width.

*Anther color.*—159C.

*Pollen color.*—NN155C.

*Pollen amount.*—Minimal.

*Number of pistils.*—1.

*Style.*—Terete, 35 mm in length and 1 mm in width.

*Style color.*—155B becoming 62C towards stigma.

*Style surface.*—Glabrous.

*Stigma shape.*—Capitate, three-lobed.

*Stigma dimensions.*—4 mm in width and 2 mm in depth.

*Stigma color.*—NN155B.

*Ovary.*—Superior, ovoid, 5 mm in length and 2.5 mm in diameter, color 145C, smooth.

Fruit: Cylindrical, 12 mm to 15 mm in length, 5 mm in diameter. Surface, glaucous. Color initially 137A becoming 185A when dry and ripe. Capsules, 2, longitudinal.

Seed: Shape, ovoid, length 1.5 mm, diameter 1 mm, color 163B to 163C, surface, rough.

Susceptibility or resistance to pests and diseases: None observed.

COMPARISON WITH PARENTAL LINE

In comparison with the female parent, the proprietary *Weigela florida* 'WG13003', 'TMWG16-04' exhibits very upright growth and heavy flowering all along its stems. The male parent is unknown, however, none of the possible male parents and the female parent exhibit such characteristics.

COMPARISON WITH CLOSEST KNOWN VARIETY

The closest comparison variety known to the inventor is *Weigela* 'TMWG16-02' (U.S. application Ser. No. 16/501,908). Whereas both 'TMWG16-04' and 'TMWG16-02' exhibit markedly upright plant habits with flowers borne along the entire length of their stems, the flowers of 'TMWG16-04' are scarlet in color, and the flowers of 'TMWG16-02' are pale to mid pink in color. In addition, 'TMWG16-04' is much later to come into flower, typically 4 weeks later than the first flowering of 'TMWG16-02'.

I claim:

1. A new and distinct cultivar of *Weigela* plant named 'TMWG16-04' as described and illustrated herein.

* * * * *